US00PP13102P2

(12) United States Plant Patent
Pieters

(10) Patent No.: US PP13,102 P2
(45) Date of Patent: Oct. 22, 2002

(54) CHRYSANTHEMUM PLANT NAMED 'FLORENCE'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,148

(22) Filed: Apr. 17, 2000

(51) Int. Cl.[7] ..... A01H 5/00
(52) U.S. Cl. ..... Plt./288
(58) Field of Search ..... Plt./288

(56) References Cited

U.S. PATENT DOCUMENTS

PP4,456 P * 8/1979 Shoesmith ..... Plt./288
PP6,402 P * 11/1988 Mack et al. ..... Plt./288
PP7,517 P * 5/1991 VandenBerg ..... Plt./288

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing flowers with white ray florets and cream disc florets.

1 Drawing Sheet

BACKGROUND OF THE INVENTION

The present invention is directed to a new and distinct variety of *Chrysanthemum morifolium*. The varietal denomination of the new chrysanthemum is 'FLORENCE'.

The new variety is a cross of two undistributed and unpatented seedlings. For convenience, the seed parent is named 'Subito' and the pollen parent is named 'Aruba'. The new variety has been asexually reproduced by vegetative cuttings in Ventura County, Calif. and the distinguishing characteristics are retained through successive generations of asexual reproduction.

SUMMARY OF THE INVENTION

'FLORENCE' is a chrysanthemum plant that produces flowers with white ray florets and cream disc florets.

COMPARISON WITH PARENTS

'FLORENCE' differs from both parents in flowering two weeks earlier under the same conditions.

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. The plants described are approximately 110 days old from a rooted cutting. 'FLORENCE' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. No susceptibility or resistance to disease has been observed. Resistance and susceptibility to insects has not been observed. Seed production has not been observed. Cold tolerance has been observed as follows: inflorescence do not show damage by cold until approximately 25° F. Further cold tolerance has not been observed. Drought tolerance has been observed in that the new variety recovers from a full wilt without damage to inflorescence or foliage. Further drought tolerance has not been observed.

ROOTING CHARACTERISTICS

Time to initiate roots: About 7 to 14 days at about 21° C.
Root description: Fine, fibrous.

PLANT

Plant type: Herbaceous perennial.
Growth habit: Mounding.
Height and width: Height about 25 cm, width about 26 cm.
Growth rate: Moderate.
Branching characteristics: Free branching, lateral branches are about 22 cm in length, about 0.5 cm in width and near 138B in color.

FOLIAGE

Arrangement: Alternate.
Compound or single: Single.
Quantity of leaves: Approximately 120 per plant of this size.
Leaf size:
*Length*.—About 7.5 cm.
*Width*.—About 5 cm.
Leaf shape: Ovate.
Leaf tip: Acuminate.
Leaf base: Attenuate.
Leaf attachment: Stalked.
Petiole: Length about 3 cm, diameter about 0.3 cm, color near 138B.
Margin type: Finely serrate.
Texture: Lightly pubescent.
Color:
*Young foliage upper side*.—Near 138A.
*Young foliage under side*.—Near 138B.
*Mature foliage upper side*.—Near 138A.
*Mature foliage under side*.—Near 138B.

Venation: Palmately net.
*Color*.—Venation upper side: Near 137C. Venation under side: Near 137D.

BLOOM

Inflorescence:
*Flowering habit*.—Induced by darkness period greater than 13.5 hours. Approximately 50 days of day length required to induce and develop blooms.
*Inflorescence form*.—Decorative.
*Natural flowering season*.—Around the second and third weeks in September in Ventura County, Calif.
*Quantity of inflorescences per stem*.—About 11.
*Inflorescence diameter*.—About 5 cm.
*Inflorescence depth*.—About 2 cm.
*Inflorescence longevity on plant*.—About 18–24 days.
*Persistence*.—Persistent.
Ray florets:
*Appearance*.—Matte.
*Texture*.—Smooth.
*Number*.—Over 200.
*Shape*.—Oblanceolate.
*Margin*.—Entire.
*Tip*.—Obtuse.
*Length*.—About 3.5 cm.
*Width*.—About 1 cm.
*Pistil*.—About 1.1 cm in length.
*Color*.—Upper side: First opening: Near 12D. Mature: Near 155D. Fading: Near 155D. Under side: First opening: Near 8D. Mature: Near 155D. Fading: Near 155D.
Disc florets:
*Appearance*.—Shiny.
*Texture*.—Smooth.
*Number*.—Over 30.
*Shape*.—Cylindric.
*Tip*.—Obtuse.
*Length*.—About 1 cm.
*Width*.—About 0.1 cm.
*Color*.—First opening: Near 13A. Mature: Near 13A. Fading: Near 13B.
Peduncle: About 0.3 cm in diameter.
*Length*.—Terminal, shortest: About 5 cm. Lateral, longest: About 9 cm.
*Color*.—Near 138A.
*Strength*.—Moderate.
*Habit*.—Erect.
Inflorescence bud:
*Length*.—About 1.2 cm.
*Diameter*.—About 1.2 cm.
*Form or shape*.—Globular.
*Color*.—Near 155D.
Involucral bracts: Length about 0.7 cm, width about 0.4 cm.
*Appearance*.—Matte.
*Texture*.—Lightly pubescent.
*Number*.—About 30 to 40.
*Shape*.—Ovate.
*Margin*.—Entire.
*Tip*.—Acute.
*Color*.—Upper side: Near 138B. Under side: Near 138B.

REPRODUCTIVE ORGANS

Ray florets:
*Pistillate*.—Pistil number: 1 per flower. Stigma shape: 2 branched. Stigma color: Near 6D. Style length: About 1 cm. Style color: Near 6D.
Disc florets:
*Pistillate*.—Pistil number: 1 per flower. Stigma shape: Cylindric. Style length: About 0.8 cm.
*Staminate*.—Stamen number: About 5. Anther shape: Tubular. Anther color: Near 6D. Pollen color: Near 4A.

What is claimed is:

1. A new and distinct chrysanthemum plant of the variety substantially as herein shown and described.

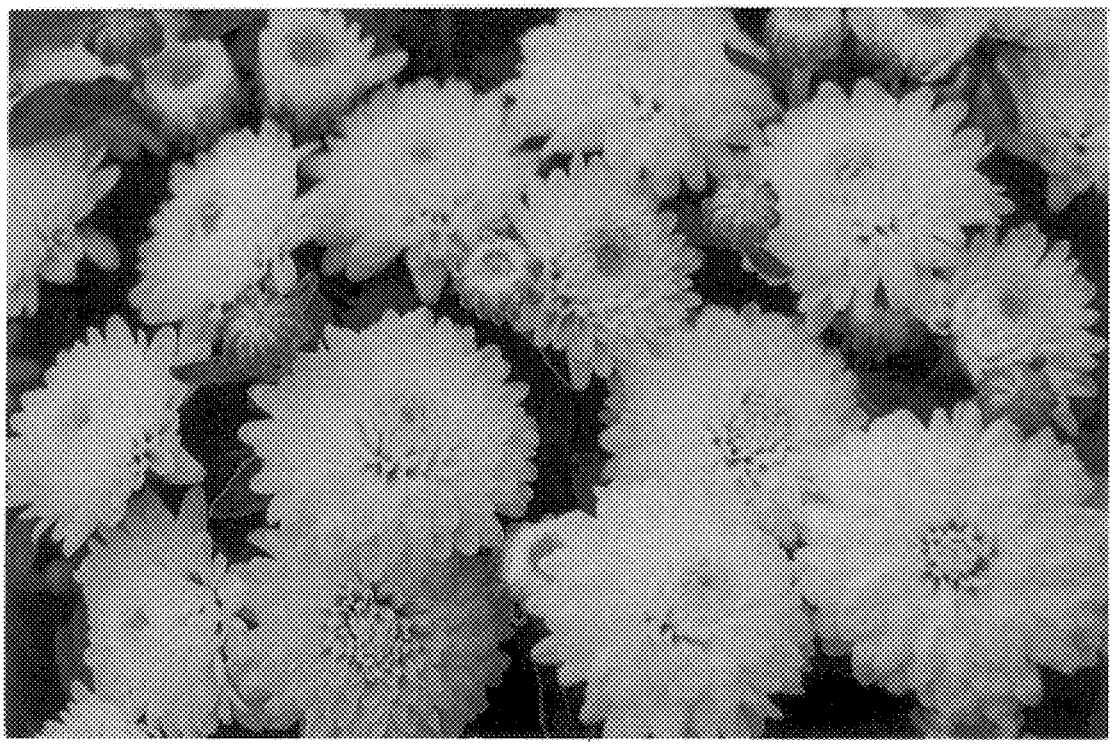

* * * * *